United States Patent [19]

Shawl et al.

[11] 4,230,877

[45] Oct. 28, 1980

[54] METHOD FOR INCREASING THE 4,4'DICARBAMATE ISOMER OF THE DIPHENYLMETHANE DICARBAMATES DURING PREPARATION THEREOF

[75] Inventors: Edward T. Shawl, Wallingford; Gerald A. Bullano, Glen Mills, both of Pa.

[73] Assignee: Atlantic Richfield Company, Los Angeles, Calif.

[21] Appl. No.: 22,749

[22] Filed: Mar. 22, 1979

[51] Int. Cl.$^2$ ............................................. C07C 125/04
[52] U.S. Cl. ..................................... 560/25; 528/242; 528/266; 560/24
[58] Field of Search ..................................... 560/25, 24

[56] References Cited

U.S. PATENT DOCUMENTS 4,146,727  3/1979  Shawl et al. ........................... 560/25

*Primary Examiner*—G. T. Breitenstein
*Attorney, Agent, or Firm*—Delbert E. McCaslin

[57] ABSTRACT

A method for increasing the 4,4' disubstituted isomer of the diphenylmethane dicarbamates produced by the acid catalyzed condensation of an N-aryl carbamic acid ester, such as ethylphenylcarbamate, with a carbonyl compound, such as formaldehyde, which comprises carrying out the condensation in a single phase system with a dilute solution of the N-aryl carbamic acid ester in an inert solvent having a dielectric constant of at least 20 at 20° C. The solvent must have good solubility for the carbamates, which carbamates are employed in the solvent at concentrations of from about 0.1 to 50 weight percent to provide a product enriched with the 4,4'-diphenylmethane dicarbamate isomer.

13 Claims, No Drawings

METHOD FOR INCREASING THE 4,4'DICARBAMATE ISOMER OF THE DIPHENYLMETHANE DICARBAMATES DURING PREPARATION THEREOF

FIELD OF THE INVENTION

The present invention relates to a process for the preparation of esters of aromatic carbamic acids (urethanes) particularly the isomeric diphenylmethane dicarbamates and including related higher homologs and derivatives by the single phase, acid catalyzed condensation of an N-aryl carbamic acid ester with formaldehyde, para-formaldehydes or trioxane in an organic solvent.

BACKGROUND OF THE INVENTION

The polymeric aromatic carbamates (polyurethanes), such as the diphenylmethane dicarbamates and related higher homologs, polymethylene polyphenyl carbamates, and especially the diethyl esters, have become increasingly important products, particularly for use in the preparation of the commercially valuable diphenylmethane diisocyanates and mixtures of diisocyanates and polyisocyanates by the thermal decomposition of such polymeric aromatic carbamates in a suitable solvent as shown, for example, in Rosenthal et al, U.S. Pat. Nos. 3,962,302 and 3,919,279.

Processes have been proposed for the preparation of polymeric aromatic carbamates (polyurethanes), as for example in Klauke et al, U.S. Pat. No. 2,946,768 and British Pat. No. 461,352, which disclose the condensation of aryl carbamic acid esters with carbonyl compounds such as aldehydes and ketones in a dilute aqueous mineral acid medium, and in co-pending U.S. application, Ser. No. 953,135, filed Oct. 20, 1978, now Pat. No. 4,162,362, which describes the condensation of N-aryl carbamic acid esters with formaldehyde, paraformaldehyde or trioxane and an organic sulfonic acid catalyst which has an acid concentration of at least 75 percent. In the Klauke et al U.S. Pat. No. 2,946,768 and British Pat. No. 461,352 processes, large amounts of undesirable N-(alkoxycarbonyl)phenylaminomethylphenyl compounds, referred to as N-benzyl compounds, are formed in addition to desired diphenylmethane dicarbamates and polymethylene polyphenyl carbamates. The rearrangement or conversion of the "N-benzyl" compounds to the desired carbamates is disclosed and fully described in co-pending U.S. application, Ser. No. 905,705, filed May 15, 1978, now U.S. Pat. No. 4,146,727.

The diphenylmethane dicarbamates in the total carbamate product resulting from any of the above noted processes generally range from about 20 to 85 percent and are a mixture of the 4,4', 2,4' and 2,2' isomers; the remainder of the carbamate product being trimers, tetramers, etc. of such compounds. Of the diphenylmethane dicarbamates in the carbamate product, the 4,4', to the 2,4' and to the 2,2' isomer ratio is approximately 4:1 and 20:1 respectively or approximately 78 percent 4,4', 18 percent 2,4' and 4 percent 2,2'. Such a product mixture is generally useful for thermal decomposition in a solvent to produce the commercially valuable diphenylmethane diisocyanates having the same isomer ratio, which isocyanates may be used to prepare urethane foam products when reacted with glycols. However, for certain applications, for example, in elastomer and coating applications or to provide greater reactivity in injection molding, it is particularly desirable to have a dicarbamate product, which when produced by the condensation processes as hereinabove noted, is enriched in or has a larger amount of the 4,4'-diphenylmethane dicarbamate isomer, which upon such decomposition in solvent provides an isocyanate enriched in the 4,4'-diphenylmethane diisocyanate.

The present invention comprises the preparation of diphenylmethane dicarbamates and polymethylene polyphenyl carbamate homologs and derivatives of these compounds by the acid catalyzed condensation of N-aryl carbamates with formaldehyde, para-formaldehyde or trioxane in a single phase inert solvent system which includes a method for controlling the disubstituted isomer to produce a product enriched in 4,4'-diphenylmethane dicarbamates, especially, the 4,4'-diphenylmethane dicarbamate, diethyl ester, as compared to the 2,4' and 2,2' isomer.

SUMMARY OF THE INVENTION

This invention relates to a method for the preparation of diphenylmethane dicarbamates and the higher molecular weight homologs, polymethylene polyphenyl carbamates, by the acid catalyzed condensation of a dilute solvent solution of an N-aryl carbamic acid ester with a carbonyl compound such as formaldehyde, paraformaldehyde or trioxane or mixture thereof in a single phase system wherein the disubstituted isomer ratio of the diphenylmethane dicarbamates produced by said condensation is controlled to yield a product enriched or increased in the 4,4'-diphenylmethane dicarbamate isomer.

The primary object of the present invention therefore is to provide an acid catalyzed condensation method for the preparation of diphenylmethane dicarbamates and the related polymethylene polyphenyl carbamates having an increased amount of the 4,4'-diphenylmethane dicarbamate of the dicarbamates produced.

Other objects and advantages of this invention will become apparent from the description of the invention which follows and from the claims.

DESCRIPTION OF THE INVENTION

In accordance with the present invention an aromatic carbamic acid ester (N-arylcarbamic acid ester) such as, for example, a lower alkyl ester of phenyl carbamic acid, particularly ethylphenylcarbamate, is contacted with formaldehyde, para-formaldehyde or trioxane at a temperature of from about ambient to about 170° C., preferably under atmospheric pressure, in the presence of an acid condensation catalyst such as for example, organic sulfonic acids, mineral acids and Lewis acids, while said N-arylcarbamic acid esters is dissolved in an inert organic solvent having a dielectric constant of at least 20 at 20° C. at a total concentration of ester in solvent of between about 0.1 to 50 weight percent preferably between 0.75 and 20 weight percent to produce a condensation product enriched in a 4,4'-diphenylmethane dicarbamate isomer.

It is a critical feature of this invention that in order to obtain a diphenylmethane dicarbamate and polymethylene polyphenyl carbamate product with enriched or increased 4,4'-diphenylmethane dicarbamate isomer the particular solvents employed must be inert in the reaction system at reaction temperatures and form a single phase system with the reactants have a dielectric constant of at least 20 at 20° C. and be employed at concentrations of between about 99.9 and 50 weight percent solvent based on the N-aryl carbamic acid ester reactant employed (0.1 to 50 weight percent ester in solvent). It has been found that during acid catalyzed condensation when the concentrations of the total N-aryl carbamic acid ester, dissolved in an inert solvent having a dielectric constant of at least 20 at 20° C., is in the range of approximately 0.1 to 50 weight percent, particularly in the case of the ethylphenylcarbamate reaction, the 4,4'-diphenylmethane dicarbamate isomer will range from about 20:1 to about 6:1 with respect to the 2,4' isomer. When the concentration of the N-aryl carbamic acid ester is greater than approximately 50 percent by weight, i.e., up to about 100 percent in the solvent or when no solvent is employed, the ratio of the 4,4' to 2,4' isomers remains essentially fixed at about 4:1. A similar but less drastic improvement is seen for the isomer ratio of the p,p'' vs. o,p'' tri-substituted trimeric carbamic acid esters also produced by the condensation reaction. When the condensation is carried out according to the invention employing dilute solutions of the N-aryl carbamate in the solvent, a ratio of 4,4'-diphenylmethane dicarbamate to 2,4'-diphenylmethane dicarbamate of approximately 20:1 may be achieved, i.e., an increase from the typical 4:1 ratio to approximately a 20:1 ratio, which corresponds to a diphenylmethane dicarbamate isomer distribution in the condensation product of 94.5 percent 4,4', 4.7 percent 2,4' and 0.8 percent 2,2'.

The isomeric diphenylmethane dicarbamates produced by the acid catalyzed condensation of the N-aryl carbamic acid esters with formaldehyde, para-formaldehyde or trioxane and controlled by the process of the instant invention are characterized by the following formulae wherein R is as hereinafter described.

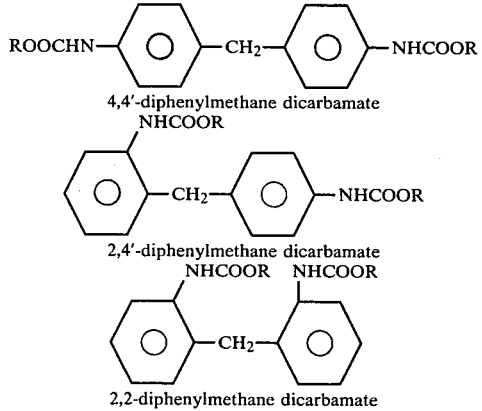

4,4'-diphenylmethane dicarbamate 2,4'-diphenylmethane dicarbamate 2,2-diphenylmethane dicarbamate The acid catalyzed condensation reaction may be carried out in any suitable reactor which is generally equipped with a means for agitation and a means for regulating temperature. A general procedure for carrying out the reaction is to charge the N-aryl carbamic acid ester and the solvent into the reaction vessel together with the desired carbonyl compound, e.g., formaldehyde, and an acid catalyst then to heat or cool the mixture, if necessary, to the desired reaction temperature for the appropriate period. Heating and/or cooling means may be employed on the interior or exterior of the reactor to maintain the temperature within the desired range. The reaction may be carried out as a batch, semi-continuous or a continuous process and the order of addition of the materials may be varied to suit the particualr apparatus employed. The reaction products are recovered and treated by any conventional method such as extraction of the acid medium with water or neutralization with an appropriate inert base and the separation of the resulting phases, as well as distillation or extraction to remove the solvent employed.

The N-aryl carbamic acid esters employed as reactants in the acid catalyzed condensation reaction must contain one or more carbamic acid ester groups, i.e., —NHCOOR groups, wherein R is an alkyl group containing up to 8 carbon atoms, an aryl group or alkyl substituted aryl group having up to 4 carbon atoms in the alkyl substitutent. The N-aryl group of the carbamic acid ester may also contain substituents such as alkyl, alkoxy, halogen, etc. on the ring. The lower alkyl esters, e.g., ethyl esters such as ethylphenylcarbamate are preferred. The N-aryl carbamic acid esters for use in the invention may be prepared for example by the process disclosed in Zajacek et al U.S. Pat. No. 3,895,054 wherein the carbamic acid esters (urethanes) are prepared by reacting an organic compound containing at least one hydroxyl group with carbon monoxide and a nitrogenous organic compound at elevated temperature and pressure in the presence of a selenium catalyst and a base and/or water, or by any other known process for preparing aromatic carbamates.

The carbonyl compounds which may be employed in the process of the invention are formaldehyde or para-formaldehyde and trioxane which are capable of producing monomeric formaldehyde in the presence of acid. The quantity of the carbonyl compound employed in the reaction relative to the N-aryl carbamic acid ester employed is based on the degree of condensation or polymerization desired in the reaction product. Generally, the molar ratio of N-aryl carbamic acid ester to the carbonyl compound, in the form of free formaldehyde in the reaction mixture, will be in the range of about 1.5 to 8:1. At the high end of the range the production of disubstituted carbamates will predominate whereas at the low end of the range the higher polymeric polymethylene polyphenyl carbamates will predominant.

The acid condensation catalyst employed and suitable for use in the present invention may be mineral acids such as sulfuric acid, Lewis acids and alkane sulfonic acids or halogenated alkane sulfonic acids having for example, up to 10 carbon atoms in the alkyl group, or an aromatic sulfonic acid. Representative sulfonic acid catalysts especially suitable for use in this invention are methane, ethane, butane, etc. sulfonic acids, trifluoromethane sulfonic acid, trichloromethane sulfonic acid, p-toluene sulfonic acid, benzene sulfonic acid, etc. The acid catalysts are generally employed in concentrations which may range from about 0.1 to 75 weight percent, preferably 5.0 to 50 weight percent of the N-aryl carbamate employed.

Solvents which are chemically inert to the components of the condensation reaction system at reaction temperatures and form a single phase system with the reactants are employed in the process of the invention. Such solvents must have a dielectric constant of at least 20 at 20° C. and be employed in the process at concentrations of between about 50 and 99.9 weight percent based on N-aryl carbamic acid ester reactant employed. Suitable solvents include, for example, the following:

| Solvent | Dielectric Constant | Recorded Temp. °C. |
|---|---|---|
| Nitrobenzene | 35.7 | 20 |
| Sulfolane | 43.3 | 30 |
| Ethylene Carbonate | 89.6 | 40 |
| Propylene Carbonate | 66.1 | 20 |
| o-nitrotoluene | 27.4 | 20 |
| m-nitrotoluene | 23.8 | 20 |
| p-nitrotoluene | 22.2 | 58 |

The dielectric constant of organic liquids, which decreases as temperature increases is defined in the CRC Handbook of Chemistry and Physics, 57th Edition, page F-99, 1976-77, and are listed for example in U.S. Department of Commerce, NBS Circular No. 514, "Table of Dielectric Constants of Pure Materials". Common solvents such as acetone, acetaldehyde and acetonitrile for example which have high dielectric constants cannot be employed in the process of the present invention due to their reactivity in the reaction system.

The reaction of the present invention will proceed at temperatures of from ambient to 170° C. It is generally preferred to operate the process at temperatures of from about 50° C. to 130° C. to obtain a convenient rate of reaction.

The process of the present invention is generally carried out at atmospheric pressure although higher pressures may be used at the higher reaction temperatures. Subatmospheric pressures may also be employed in the process, if desirable.

The reaction is time is generally dependent upon the N-aryl carbamate being reacted, the reaction temperature and on the amount and type of acid condensation catalyst being employed and will vary depending on whether the process is continuous or batch but will generally range between about 2 minutes and several hours.

Although the process of the present invention is primarily directed to the condensation of ethylphenylcarbamate (EPC) and increase of the 4,4'-diphenylmethane dicarbamate, diethyl ester, isomer it is not intended that the process be limited to such carbamate condensation and those skilled in the art will recognize that the present process is broadly applicable to the condensation of other N-aryl carbamic acid esters such as methylphenylcarbamate, ethyl-N-(2-methylphenyl)carbamate, butylphenylcarbamate, etc. and control and increase of the respective 4,4' isomer of the diphenylmethane dicarbamates produced.

The following Examples are provided to illustrate the invention in accordance with the principles of this invention but are not to be construed as limiting the invention in any way except as indicated by the appended claims.

In the Examples which follow, the reactions were run in a 300 ml., or appropriate size, three neck glass reaction flask fitted with a mechanical stirrer, reflux condenser and thermometer. The reactants were charged to the reaction flask and the flask immersed into a constant temperature oil bath. At the end of the reaction time, water was added to the flask to quench the reaction and extract the acid catalyst medium. Solvent was removed by distillation or water extraction. Conversion of the N-aryl carbamate charged and condensation product yield and polymer distribution, particularly the disubstituted isomer ratios, were determined by high speed liquid chromatography.

EXAMPLE 1

A number of batch condensation runs were carried out with various dilutions of ethylphenylcarbamate in a nitrobenzene solvent. The ethylphenylcarbamate to HCHO (trioxane) ratio of 2.1:1 provided a disubstituted isomer content of 55 percent of the total carbamate product. The ethylphenylcarbamate (30 g.) was charged to the reaction flask as a nitrobenzene solution. Trioxane (2.60 g.) and 96 percent sulfuric acid were added and the mixture heated to 80° C. for the periods indicated. The condensation product was water washed. The nitrobenzene solvent was then removed by vacuum distillation. The results showing condensation reaction conditions, selectivities and 4,4' to 2,4' isomers ratios are summarized in Table 1. Run Nos. 10, 11 and 12 are comparative runs with the ethylphenylcarbamate (EPC) in nitrobenzene being 100 (no solvent), 84 percent and 65 percent respectively.

TABLE 1

| Run No. | Time (min.) | Weight % EPC[1] in Feed | Mol/mol EPC/Acid | Weight % Acid (Total Mix) | % Conversion EPC | % Selectivity to Di-[2] Urethane | % Selectivity to N-Benzyl Compounds | Dicarbamate Isomer Ratio (4,4'/2,4') |
|---|---|---|---|---|---|---|---|---|
| 1 | 60 | 50.0 | 1.85 | 12.0 | 79 | 56 | 0.3 | 4.2 |
| 2 | 55 | 25.0 | 1.85 | 7.3 | 76 | 56 | 0.9 | 6.0 |
| 3 | 55 | 10.0 | 1.85 | 3.1 | 79 | 58 | 0.04 | 7.8 |
| 4 | 55 | 5.0 | 1.85 | 1.6 | 79 | 48 | 1.0 | 10.4 |
| 5 | 50 | 5.0 | 1.55 | 1.9 | 85 | 56 | 0.7 | 10.5 |
| 6 | 60 | 0.84 | 1.55 | 0.32 | 79 | 53 | 0.4 | 17.3 |
| 7 | 55 | 0.84 | 0.76 | 0.64 | 86 | 53 | 0.0 | 17.6 |
| 8 | 60 | 0.84 | 0.38 | 1.26 | 83 | 48 | 0.0 | 11.2 |
| 9 | 40 | 0.84 | 0.39 | 1.26 | 81 | 45 | 0.0 | 10.9 |
| 10 | 80 | 100.0 | 1.85 | 23.5 | 79 | 54 | 0.0 | 3.6 |
| 11 | 90 | 84.0 | 1.85 | 20.7 | 79 | 52 | 0.0 | 3.6 |
| 12 | 60 | 65.0 | 1.85 | 17.0 | 80 | 50 | 0.0 | 3.8 |

[1] ethylphenylcarbamate
[2] diphenylmethane dicarbamates

EXAMPLE 2

The procedure and conditions of Example 1 were repeated with a 4.7, 1.0 and 50 percent ethylphenylcarbamate (30 g.) in nitrobenzene solvent except that the EPC to HCHO (trioxane 1.24 g.) ratio was 4.4:1 providing a carbamate product with a disubstituted isomer (4,4', 2,4' and 2,2') content of 80 percent. The results are summarized in Table 2.

TABLE 2

| Run No. | Time (min.) | Weight % EPC in Feed | Mol/mol EPC/Acid | Weight % Acid (Total Mix) | % Conversion EPC | % Selectivity to Di-Urethane | % Selectivity to N-Benzyl Compounds | Dicarbamate Isomer Ratio (4,4'/2,4') |
| --- | --- | --- | --- | --- | --- | --- | --- | --- |
| 1 | 55 | 4.7 | 2.23 | 1.25 | 49 | 85 | 0.1 | 9.4 |
| 2 | 60 | 1.0 | 2.23 | 0.27 | 47 | 87 | 0.2 | 16.0 |
| 3 | 60 | 50.0 | 1.85 | 12.0 | 49 | 84 | 0.0 | 3.9 |

EXAMPLE 3

Runs were made with various dilutions of ethylphenylcarbamate in sulfolane (tetramethylene sulfone or tetrahydrothiophene-1,1-dioxide) as a solvent. The ethylphenylcarbamate (30 g.) was charged to the reactor as a sulfolane solution. Trioxane (2.73 g.) and anhydrous methane sulfonic acid were added and the mixture heated to 100° C. for 50 minutes. The ethylphenylcarbamate to HCHO ratio was 2.0:1. The condensation dicarbamate product was extracted with toluene and water washed to remove acid and the sulfolane solvent. The conditions and analytical results are summarized in Table 3 below.

TABLE 3

| Run No. | Weight % EPC in Feed | Mol/mol EPC/Acid | Weight % Acid (Total Mix) | % Conversion EPC | % Selectivity to Di-Urethane | % Selectivity to N-Benzyl Compounds | Dicarbamate Isomer Ratio (4,4'/2,4') |
| --- | --- | --- | --- | --- | --- | --- | --- |
| 1 | 50 | 0.80 | 25.8 | 86 | 48 | 0.0 | 5.18 |
| 2 | 30 | 0.80 | 15.4 | 84 | 50 | 0.8 | 7.8 |
| 3 | 5 | 0.80 | 3.5 | 85 | 52 | 2.5 | 10.8 |
| 4 | 1 | 0.80 | 0.72 | 68 | 53 | 7.8 | 14.6 |

EXAMPLE 4

Runs were carried out with various dilutions of 3.51 g. of butylphenylcarbamate (BPC) in a nitrobenzene solvent. A butylphenylcarbamate to HCHO (50 percent aqueous formaldehyde) ratio of 2.0:1 was employed. The butylphenylcarbamate was charged to the reaction flask as a nitrobenzene solution and 5.46 g. formaldehyde along with anhydrous trifluoromethane sulfonic acid was added. The mixture was heated to 80° C. for one hour after which the condensation product was water washed and the nitrobenzene solvent removed by distillation. The reaction conditions and analytical results are summarized in Table 4.

TABLE 4

| Run No. | % BPC[1] in Feed | Mol/mol BPC/Acid | Weight % Acid (Total Mix) | % Conversion BPC | % Selectivity to Di-Urethane | % Selectivity to N-Benzyl Compounds | Dicarbamate Isomer Ratio (4,4'/2,4') |
| --- | --- | --- | --- | --- | --- | --- | --- |
| 1 | 50 | 3.6 | 9.4 | 88 | 49 | 0.0 | 4.1 |
| 2 | 25 | 3.6 | 5.0 | 86 | 53 | 0.3 | 6.2 |
| 3 | 5 | 2.5 | 1.5 | 87 | 52 | 0.1 | 10.0 |
| 4 | 1 | 2.5 | 0.30 | 84 | 55 | 0.5 | 15.5 |

[1] butylphenylcarbamate

EXAMPLE 5

Runs were carried out with various dilutions of ethylphenylcarbamate in an ethylene carbonate solvent. The ethylphenylcarbamate (30 g.) was charged to the reactor as an ethylene carbonate solution. 2.73 g. of trioxane and anhydrous methane sulfonic acid were added to the mixture and the mixture heated (Run No. 1 at 80° C. and Runs Nos. 2 and 3 at 100° C.) for a period to effect condensation. The ethylphenylcarbamate to HCHO ratio was 2.0:1. The dicarbamate condensation product was extracted with toluene and water washed to remove acid and the ethylene carbonate solvent. The reaction conditions and analytical results are given in Table 5 below.

TABLE 5

| Run No. | Time (min.) | Weight % EPC in Feed | Mol/mol EPC/Acid | Weight % Acid (Total Mix) | % Conversion EPC | % Selectivity to Di-Urethane | % Selectivity to N-Benzyl Compounds | Dicarbamate Isomer Ratio (4,4'/2,4') |
| --- | --- | --- | --- | --- | --- | --- | --- | --- |
| 1 | 50 | 50.0 | 0.80 | 25.8 | 88 | 49 | 0.7 | 6.0 |
| 2 | 70 | 5.0 | 0.80 | 3.5 | 87 | 50 | 0.4 | 9.2 |
| 3 | 65 | 0.5 | 0.80 | 0.36 | 80 | 50 | 0.5 | 15.0 |

We claim:

1. A method for the preparation of diphenylmethane dicarbamates and polymethylene polyphenyl carbamates having an increased amount of 4,4'-diphenylmethane dicarbamate isomer in the total diphenylmethane dicarbamate produced which comprises reactng in a single phase system an N-aryl carbamic acid ester with a carbonyl compound selected from formaldehyde, para-formaldehyde or trioxane or mixtures thereof, at a temperature of from about ambient to about 170° C. in the presence of a mineral acid condensation catalyst while said N-aryl carbamic acid ester is dissolved in an inert organic solvent having a dielectric constant of at least 20 at 20° C. and at a concentration of N-aryl carbamic acid ester in said solvent of from 0.1 to 50 weight percent and recovering the desired carbamates.

2. A method according to claim 1 wherein the N-aryl carbamic acid ester is selected from the group consisting of methylphenylcarbamate, ethylphenylcarbamate and butylphenylcarbamate.

3. A method according to claim 2 wherein the N-aryl carbamic acid ester is ethylphenylcarbamate.

4. The method according to claim 1 wherein the catalyst is sulfuric acid.

5. A method according to claim 1 wherein the reaction is carried out at a temperature in the range of from about 50° C. to 130° C.

6. A method according to claim 1 wherein the carbonyl compound is trioxane.

7. A method according to claim 1 wherein the carbonyl compound is aqueous formaldehyde.

8. A method according to claim 1 wherein the inert organic solvent is selected from the group consisting of nitrobenzene, sulfolane, ethylene carbonate, propylene carbonate, and o-, m-, and p-nitrotoluene.

9. A method according to claim 8 wherein the solvent is nitrobenzene.

10. A method according to claim 8 wherein the solvent is sulfolane.

11. A method according to claim 8 wherein the solvent is ethylene carbonate.

12. A method according to claim 1 wherein the concentration of the N-aryl carbamic acid ester in solvent is 0.75–20 weight percent.

13. A method for the preparation of a diphenylmethane dicarbamate, diethyl ester, and polymethylene polyphenyl carbamates, ethyl esters, having an increased amount of 4,4'-diphenylmethane dicarbamate, diethyl ester in the total diphenylmethane dicarbamate produced which comprises reacting in a single phase system at atmospheric pressure ethylphenylcarbamate with trioxane at a temperature of from about 50° C. to 130° C. in the presence of from 5.0 to 50 weight percent of the ethylphenylcarbamate employed of a sulfuric acid condensation catalyst while said ethylphenylcarbamate is dissolved in an inert organic solvent having a dielectric constant of at least 20 at 20° C. and a concentration of ethylphenylcarbamate in said solvent of 0.75 to 20 weight percent and recovering the desired diphenylmethane dicarbamate.

* * * * *